United States Patent [19]

Tu

[11] Patent Number: 4,758,235
[45] Date of Patent: Jul. 19, 1988

[54] CARDIOPULMONARY RESUSCITATION MEDICATION ASSEMBLY

[76] Inventor: Ho C. Tu, 241 NE. 199th La., North Miami Beach, Fla. 33179

[21] Appl. No.: 53,834

[22] Filed: May 26, 1987

[51] Int. Cl.⁴ ............................................. A61M 5/005
[52] U.S. Cl. .................................... 604/248; 251/904; 251/311; 604/189
[58] Field of Search .................... 604/32, 189, 80–81, 604/248, 93; 251/904, 311

[56] References Cited

U.S. PATENT DOCUMENTS

| | | | |
|---|---|---|---|
| 2,854,027 | 9/1958 | Kaiser et al. | 251/904 |
| 2,902,253 | 9/1959 | Page | 251/311 |
| 3,437,243 | 4/1969 | Farnsworth | 604/189 |
| 3,885,562 | 5/1975 | Lampkin | 604/189 |
| 4,219,021 | 8/1980 | Fink | 604/93 |
| 4,256,132 | 3/1981 | Gunter | 604/189 |
| 4,604,093 | 8/1986 | Brown et al. | 604/248 |

Primary Examiner—Stephen C. Pellegrino
Assistant Examiner—Colleen Reilly
Attorney, Agent, or Firm—Alvin S. Blum

[57] ABSTRACT

Apparatus is provided for intravenous administration of a series of solutions for cardiopulmonary resuscitation. Each solution is in a separate syringe held in place on a base plate. All syringes are connected at the same time to a single stopcock with multiple inlets and a single outlet for connection via tubing to a needle in the patient's vein. A selector handle on the stopcock is rotated to a particle inlet to select the solution in a particular syringe. The assembly eliminates the changing of syringes, the confusion and errors, and the need for assistance of the prior apparatus and speeds up the administration of the medications to make the treatment more effective, and, more importantly, reduces the risk of bacterial contamination.

15 Claims, 2 Drawing Sheets

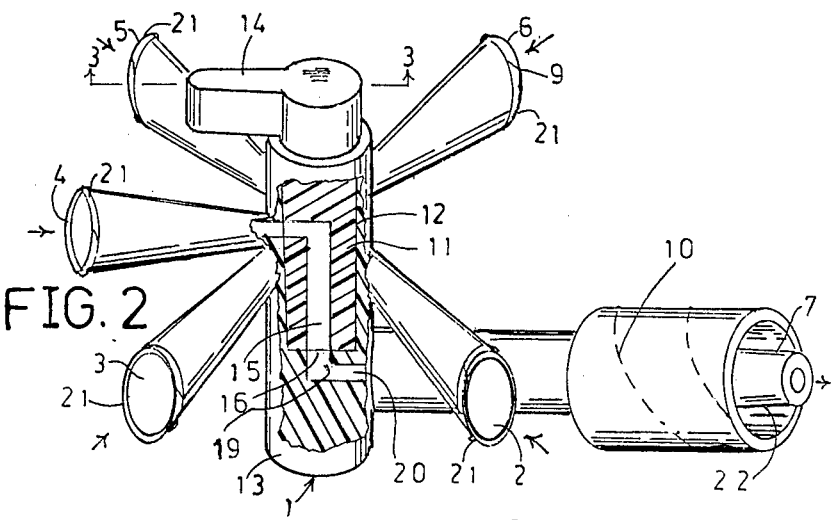
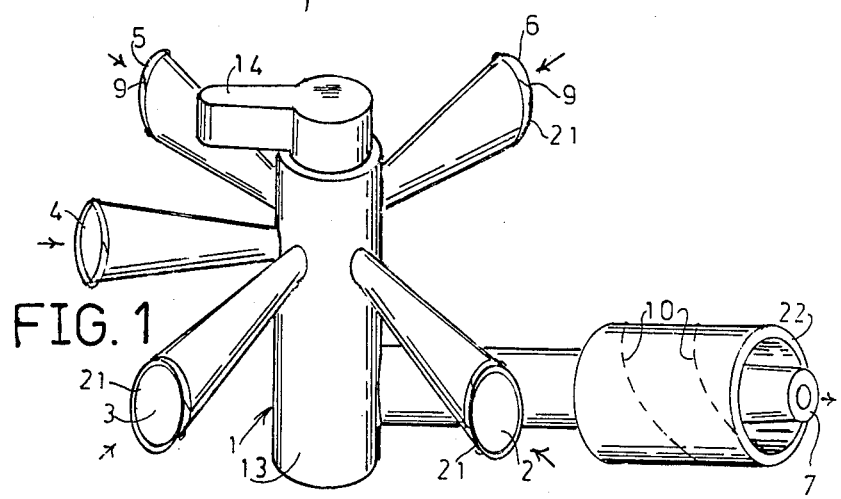
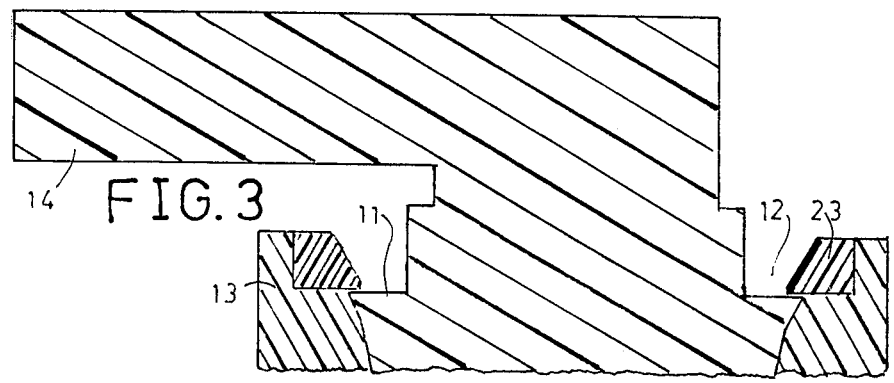

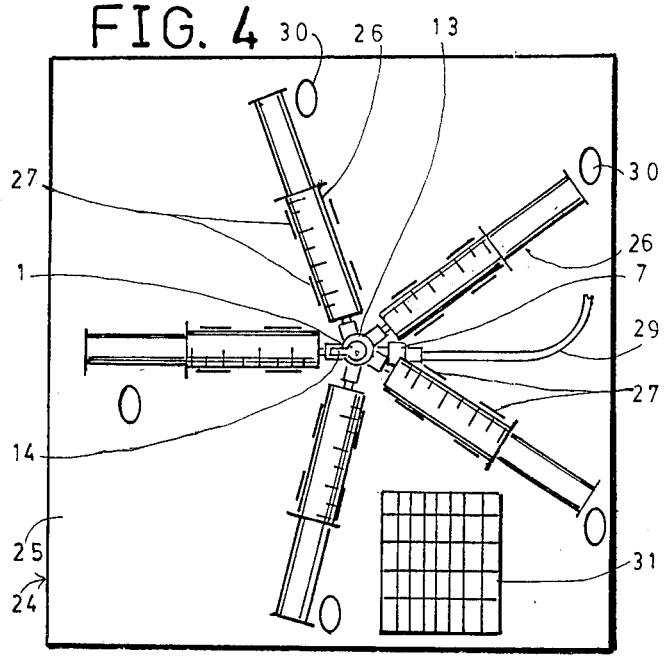
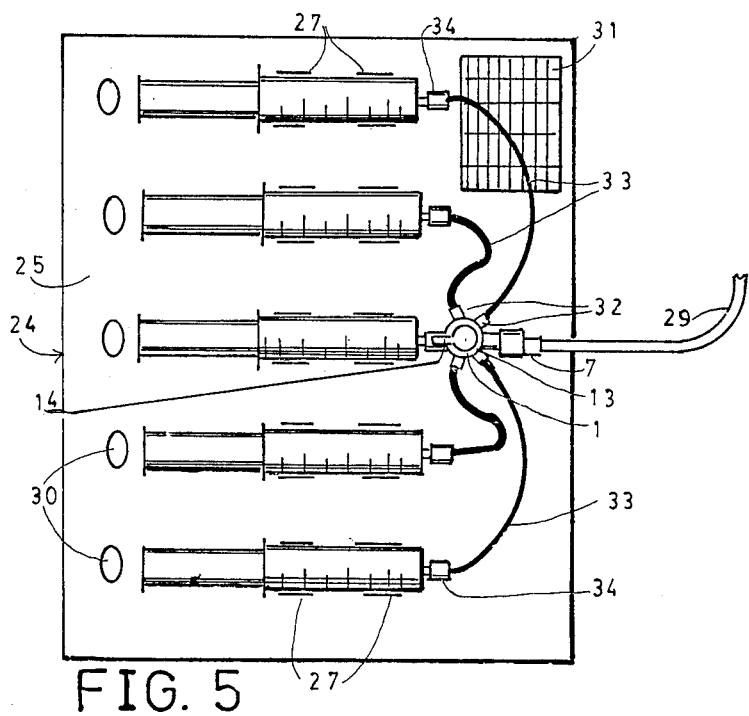

CARDIOPULMONARY RESUSCITATION MEDICATION ASSEMBLY

This invention relates to a system for facilitating the intravenous administration of a series of different solutions, and more particularly to a system for the rapid intravenous administration of a series of medications in the emergency medical treatment known as cardiopulmonary resuscitation.

Treatment of a patient experiencing cardiopulmonary failure, as evidenced by loss of blood pressure, reduction or absence of heartbeat, hypoxemia and the like oridnarly includes the intravenous injection of certain medications in rapid succession. Medications commonly used include: calcium gluconate; atropine; epinephrine; lidocaine; and bicarbonate, although others may be employed to suit the particular situation.

These solutions are oridnarily administered through a tube to a single needle inserted into a vein, and the tubing is flushed with saline between each solution. The needle tubing is connected to the outlet of a stopcock having two inlets and three operating positions. There is an operating position connecting the first inlet to the outlet; a second position connecting the second inlet to the outlet; and a third position closing off the outlet from both inlets. One inlet is connected to a source of saline for flushing. This may be a bag or a syringe. Syringes holding the above medications are fitted onto the second inlet as required for injecting the appropriate amount (dose) of each of the medications. This involves switching the stopcock operating position between inlets to flush with saline between each dose and to close off the second inlet while changing syringes between medications.

The physician performing the procedure calls out the medication and dose and one or more assistants fill the syringes from vials and hand them to the physician in correct order.

This is often a chaotic environment. Other operators may be treating the patient at the same time, such as inhalation therapists restoring respiration and others involved in converting the heart beat. Errors in dosage, confusion of the identity of the medication and delays in administration can be fatal, but they can easily occur in the environment in which this treatment is often required. Furthermore, the extra assistants required in handling the doses only add to the confusion and reduce the chances of success when inadequate staff is available. Changing syringes also increases the risk of bacterial contamination.

SUMMARY OF THE INVENTION

It is, accordingly, an object of the invention to provide a system that makes available in an emergency a plurality of cardiopulmonary resuscitation medications for sequential intravenous administration with flushing between doses that can be controlled by the administering physician without requiring the assistance of other in dosage supply and measurement.

It is yet another object of the invention to provide an assembly that does not require the changing of syringes between injections, and that reduces the risk of contamination.

It is yet another object to provide an assembly of apparatus that is all in place and ready for emergency use that appropriately identifies and locates each medication to reduce errors and speed operation.

It is yet another object to provide dosage data recommendations as part of the assembly to further reduce errors.

It is yet another object to provide an assembly that requires less skill and dexterity to facilitate treatment.

The assembly includes a support plate for holding the stopcock and syringes and connecting devices in operational readiness, and which may serve as a delivery and storage package. The support may include labels identifying the various components and a dosage recommendation chart. The stopcock is of special construction to permit the sequential administrations with flushings in between each one while all of the syringes are connected to the stopcock by a simple switching of one control on the stopcock. The operator requires no assistance because all of the solutions are in place at all times and the operator controls the dosage by the volume of each solution administered.

These and other objects and advantages of the invention will become evident from the following detailed descriptions with reference to the appended drawings.

BRIEF DESCRIPTION OF THE DRAWINGS

FIG. 1 illustrates a five inlet stopcock with a common outlet in perspective view.

FIG. 2 illustrates the stopcock of FIG. 1 with a portion broken away to show internal structure, in section, through the diameter at line 3—3.

FIG. 3 shows a front elevation sectional view of the upper portion of the stopcock of FIG. 2 taken through the line 3—3 to illustrate the plug-tightening means.

FIG. 4 is a plan view of the assembly of the invention with a circular array of syringes.

FIG. 5 is a plan view of the assembly of the invention with a parallel array of syringes.

DETAILED DESCRIPTION OF PREFERRED EMBODIMENTS OF THE INVENTION

Referring now first to FIGS. 1-3, a stopcock 1 has five inlets 2-6 and a single outlet 7. Each inlet terminates in a standard female luer lock fitting 21 for securely engaging a syringe, and the outlet terminates in a standard male luer lock fitting 22. These are well known in the industry for providing a leak-tight fitting wherein a spiral projection 9 on the female fitting 21 threads into a thread groove 10 in the interior of the cylinder surrounding the male fitting 22 for pulling male and female members securely together.

The five inlets 2-6 are in a common plane, spaced 72° apart to provide maximum sealing surface between openings. As is shown in FIG. 2, the plug 11 makes a liquid tight seal in recess 12 of barrel 13 at all inlet positions except when the manual position selection means 14 aligns an inlet with the radial hole 17 in plug 11. The outlet 7 is in a plane below the plane of the inlets. The stopcock 1 is comprised of a tapered plug 11 which rotates in a closely fitting tapered recess 12 in barrel 13. The plug 11 has a handle 14 for rotating the plug between the five inlet positions. The plub has an axial hole 15 extending through the plug bottom 16. A single radial hole 17 connects at one end to the axial hole 15 and at the other end extends to the surface of the plug to connect to any one of the five inlet holes in the brrel 13, depending upon the position of handle 14. The axial hole 15 in plug 11 is always in registry with axial hole 19 in barrel 13. A single radial hole 20 in barrel 13 connects at one end with the axial hole 19 and at the other end forms the liquid passage in the outlet 7.

To maintain a liquid-tight, rotatable seal between the tapered plug 11 and the tapered recess 12 in barrel 13, the two surfaces are made very smooth and of closely matching tapers. The plug is made of a resilient and lubricous material as exemplified by the fluorocarbon plastics. To maintain the plug tightly in the recess, the mechanism shown in the detail of FIG. 3 may be employed. A tapered locking collar 23 at the top of barrel 13 forces the plug 11 into the tapered recess 12 in barrel 14 when tapered plug 11 is forced into and past the locking collar 23 with a snap-in action. The collar 23 may be molded separately and fastened to the barrel to form a tapered recess with a locking top.

Referring now to FIG. 4, a complete assembly 24 includes a base plate 25 to which stopcock 1 is securely fastened so that handle 14 may be turned without holding the barrel 13. Syringes 26 are secured to plate 25 by syringe holding clips 27. Each syringe may be provided filled with solution and sealed, and in proper position on the plate. The seal may be removed and the syringe then engaged in its respective inlet 2-6 on the stopcock ready for use. A tube 29 leading from a needle in a vein generally has a standard female luer fitting to fit into the outlet 7 of the stopcock. A label 30 is affixed to plate 25 at each syringe, identifying the contents of that syringe and a table 31 is also affixed to plate 25 giving the recommended dose of each of the four medications for a number of different body weights to further reduce the chances of errors in administration of the medications.

The circular array of FIG. 4 takes up a good deal of space, and some of the syringes are at an awkward angle for use. The syringes are arranged in parallel in the assembly of FIG. 5 to occupy less space and to provide all of the syringes in the same orientation for easier handling. The stopcock 1 for this embodiment has four of the inlets terminating in sleeves 32 into which tubes 33 are secured. The tubes 33 terminate in female luer fittings 34 that are secured to plate 25 for receiving syringes 26. The tubes 33 have a small internal volume relative to the dose. Again labels 30 identifying the medications and dosage/weight chart 31 help prevent errors in administration of the medications.

For use, the syringes 26 are unsealed and fitted into the fittings 34. The patient's intravenous tube 29 is fitted into the outlet 7 of the stopcock 1. The stopcock handle 14 is turned to the saline syringe and the tube filled with saline. The tube is connected to the needle in the vein. The stopcock handle is next turned to the atropine syringe and the appropriate volume is dispensed. The handle is turned back to the saline syringe and enough saline is administered to flush the system. The stopcock handle is next turned to the epinephrine syringe and the appropriate volume is dispensed. The handle is turned back to the saline syringe and enough saline to flush the system is administered. The procedure continues through the administration of lidocaine and bicarbonate. If necessary, the procedure is repeated a second and even a third time. There is no moving about and passing around syringes and calling out medications and doses. The physician administering the medications is in full control at all times. Because everything is at hand, treatment can be started and completed more rapidly. This type of treatment calls for very rapid response for what is often a life threatening emergency.

An assembly for five syringes is shown, however, the general principle may be applied to an assembly of four, six, seven or more syringes as required. Medical progress may change the nature of the medications as well as their number.

The above disclosed invention has a number of particular features which should preferably be employed in combination although each is useful separately without departure from the scope of the invention. While I have shown and described the preferred embodiments of my invention, it will be understood that the invention may be embodied otherwise than as herein specifically illustrated or described, and that certain changes in the form and arrangement of parts and the specific manner of practicing the invention may be made within the underlying idea or principles of the invention within the scope of the appended claims.

I claim:

1. An assembly for facilitating the intravenous administration of a series of medications for cardiopulmonary resuscitation, comprising:

a supporting base means for supporting all the necessary elements of the administration in position for most effective use; a plurality of syringe holding means connected to the surface of said base means for holding a plurality of syringes containing said medications and a flushing solution in convenient positions ready for use;

a stopcock held in position on the surface of said base means, said stopcock having a plurality of inlet means, one for each of said medications and one for said flushing solution, said inlet means including syringe connecting means for connecting said stopcock to said syringe in leak-tight connection;

said stopcock further having a single outlet means, said outlet means including tubing connection means for connecting said outlet to intravenous tubing communicating with the vein of a patient, said stopcock further including manual position selection means for selectively connecting one of said inlet means with said outlet means so that a medication from a selected syringe can be injected into said patient by simple manual operation of said selection means said stopcock including means sealing said outlet means from said inlet means when said position selection means is not connecting one of said selected inlet means with said outlet means.

2. The assembly of claim 1, further including a plurality of syringe identification label means connected to said base means and located with relation to said syringe holding means to identify appropriately the contents of each syringe that will be placed on said base means to reduce errors.

3. The assembly of claim 1, further including a chart of recommended dosages for said medications for different body weights affixed to the surface of said base means to reduce errors.

4. The assembly of claim 2, further including syringes filled with said medications and said flushing solution and held in correct locations by said syringe holding means to provide a package ready for use in an emergency, said syringes including syringe sealing means for sealing in the syringe contents during shipment.

5. In the assembly of claim 1, said stopcock further comprising a tapered inner plug means and an outer barrel means, said plug means connected to said selection means at the upper end of said plug means, said plug means rotatably and sealably engaged in a tapered recess in said barrel means; said barrel means having said plurality of inlet means arranged radially in a common plane, said barrel means further having said outlet means arranged radially at a plane below said inlet means, sid plug means including an axial bore extending through the bottom of said plug means at a first end, said bore connecting with a radial bore at a second end, said radial bore extending from said axial bore to the tapered lateral surface of said plug at a level corresponding to said common plane of said inlet means when said plug is sealably seated in said barrel so that said bore communicates with the inner fluid passage of each inlet means when said plug is selectively rotated about its longitudinal axis by said selection means, said barrel further including an axial bore below said tapered recess that is in registry with said axial bore in said plug means, said axial bore in said barrel is connected to a radial bore extending into said outlet means so that a fluid passage may be established from any one of said inlet means through said outlet means by the rotation of said selection means for the intravenous injection of the contents of the syringe connected to said inlet means.

6. The assembly of claim 5, further including plug tightening means said plug tightening means biasing said tapered plug into sealing relationship with said tapered recess in said barrel.

7. In the assembly of claim 6, said plug tightening means including a locking collar means connected to the upper end of said barrel.

8. In the assembly of claim 5, said plug is composed of a lubricous, resilient material for enhanced rotating and sealing.

9. The plug of claim 8 composed of a fluorocarbon plastic.

10. In the assembly of claim 1, said syringe connecting means including tubing means connecting said stopcock to said syringe connecting means so that said syringe holding means and said syringes may be arranged on said base means in substantially parallel array for more compact arrangement and easier handling.

11. A stopcock for facilitating the intravenous administration of a series of medications for injection into a needle in a patient's vein for cardiopulmonary resuscitation, comprising:

a tapered inner plug means;

a position selection handle connected to the top of said plug means for rotating said plug means;

an outer barrel means having an inner recess for receiving said plug means, said recess having an open top and a closed bottom, said recess having a taper matching said plug means to provide a rotating seal of said plug means in said recess;

said barrel means including a plurality of syringe-connecting inlet means arranged radially in a common plane about the longitudinal axis of said barrel means, each of said inlet means including a fluid passage extending to said recess, said barrel means further including an axial bore extending from said bottom of said recess to a radial bore extending outwardly to an outlet means with tubing connecting means for connecting to intravenous tubing that is connected to said needle in said patient's vein;

said plug means including a fluid passage therethrough comprised of an axial bore extending from the bottom of said plug where said bore is in registry with the axial bore of said barrel means up to the level of said inlet means in said barrel means, said bore in said plug means then extending radially to the outer surface of said plug means where it may be positioned in registry with the fluid passage of any particular inlet means by rotation of said position selection handle so that a fluid passage may be established from any selected inlet means to said outlet means;

and plug tightening means connected to the top of said barrel means for forcing said plug means tightly into said recess to ensure liquid tight sealing of said plug means in said recess in said barrel.

12. In the stopcock of claim 11, said plug tightening means including a locking collar means.

13. In the stopcock of claim 12 said locking collar means including a tapered surface for snap-in fitting of said plug means.

14. In the stopcock of claim 11, said plug means is composed of a resilient, lubricous material for enhanced sealing and rotating.

15. The plug means of claim 14 composed of a fluorocarbon plastic.

* * * * *